US00PP28694P2

(12) United States Plant Patent
Van Swieten

(10) Patent No.: US PP28,694 P2
(45) Date of Patent: Nov. 28, 2017

(54) ***PHALAENOPSIS* ORCHID PLANT NAMED 'PHALDUECH'**

(50) Latin Name: ***Phalaenopsis* hybrid**
Varietal Denomination: PHALDUECH

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 15/330,506

(22) Filed: Sep. 29, 2016

(51) Int. Cl.
*A01H 5/02* (2006.01)

(52) U.S. Cl.
USPC ..... Plt./220

(58) Field of Classification Search
USPC ..... Plt./311
See application file for complete search history.

*Primary Examiner* — Annette H Para
(74) *Attorney, Agent, or Firm* — Jondle & Associates, P.C.

(57) ABSTRACT

A new and distinct variety of *Phalaenopsis* plant named 'PHALDUECH', particularly characterized by having small white flowers, 1 to 3 peduncles that are medium long and sturdy, leaves that are narrow oblong, and is propagated by meristem tissue culture, is disclosed.

3 Drawing Sheets

Genus and species: *Phalaenopsis* hybrid.
Variety denomination: 'PHALDUECH'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALDUECH'.

The new *Phalaenopsis* plant is a product of a planned breeding program conducted by the inventor in Bleiswijk, The Netherlands. The objective of this breeding program was to create a new *Phalaenopsis* plant with many small white flowers, suitable for potted plant production.

The new *Phalaenopsis* plant 'PHALDUECH' is a result of cross-pollination made by the inventor in January 2006 in Bleiswijk, The Netherlands of the proprietary female, or seed parent, *Phalaenopsis* hybrid '01-0274' (unpatented) with the proprietary male, or pollen parent, *Phalaenopsis* hybrid '22481-01' (unpatented).

The new *Phalaenopsis* was selected by the inventor as a single plant within the progeny of the stated cross-pollination in a controlled greenhouse in Bleiswijk, The Netherlands in March 2009. Asexual reproduction of the new *Phalaenopsis* plant by meristem tissue culture since 2011 in Bleiswijk, The Netherlands, has demonstrated that the new variety reproduces true to type with all of the characteristics, as herein described, firmly fixed and retained through successive generations.

Plant Breeder's Rights for this variety have been applied for in Europe on Apr. 18, 2016. 'PHALDUECH' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Bleiswijk, The Netherlands and can be used to distinguish 'PHALDUECH' as a new and distinct variety of *Phalaenopsis* plant.

1) Small white flowers;
2) 1 to 3 peduncles;
3) Peduncle is medium long and sturdy; and
4) Shape of the leaf is narrow oblong.

DESCRIPTION OF THE PHOTOGRAPHS

This new *Phalaenopsis* plant is illustrated by the accompanying photographs which show the overall plant habit including blooms, buds and foliage of the plant; the colors shown are as true as can be reasonably obtained by conventional photographic procedures. The photographs were taken in a greenhouse in Bleiswijk, The Netherlands, from 50-week old plants in August 2016. Colors in the photographs may differ from the color values cited in the detailed botanical description, which accurately describe the actual colors of the new variety.

DESCRIPTION OF THE NEW VARIETY

Figure 1:
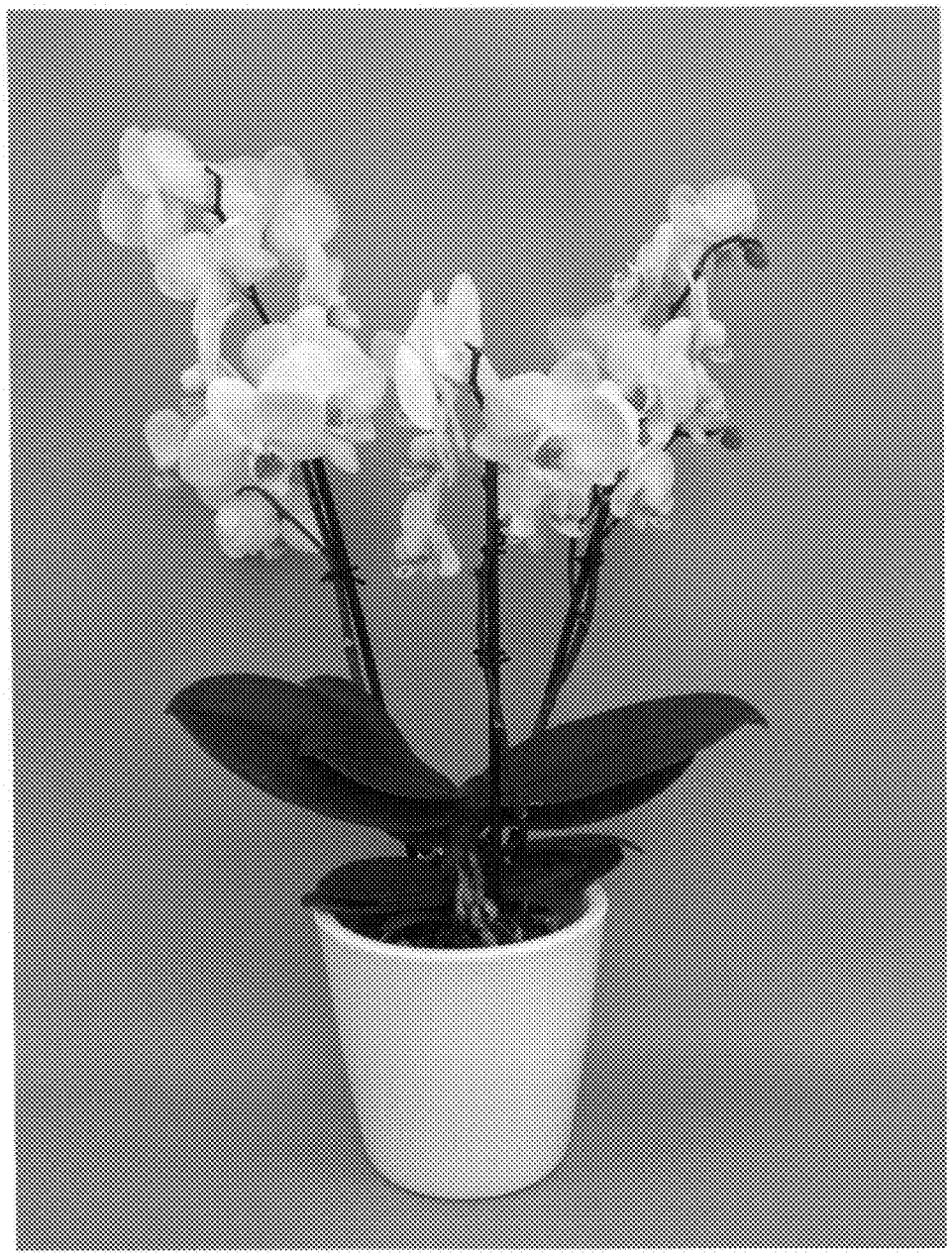
FIG. 1 shows the overall plant habit, including blooms, buds and foliage of 'PHALDUECH'.
Figure 2:
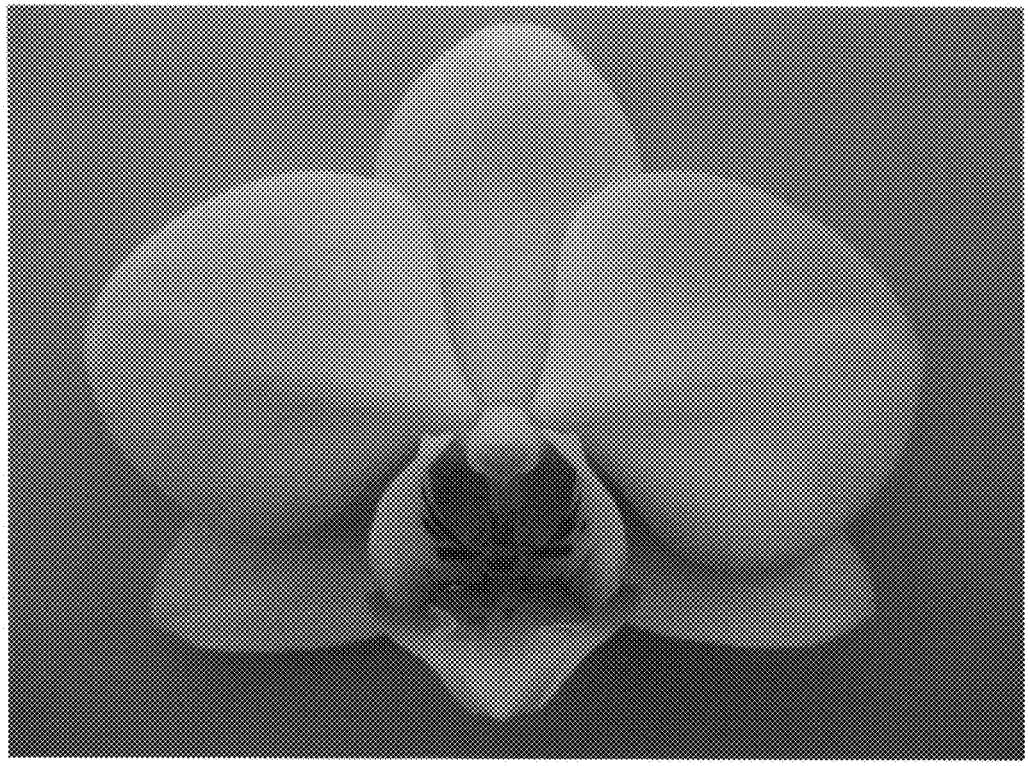
FIG. 2 shows a close-up of a flower of 'PHALDUECH'.
Figure 3:
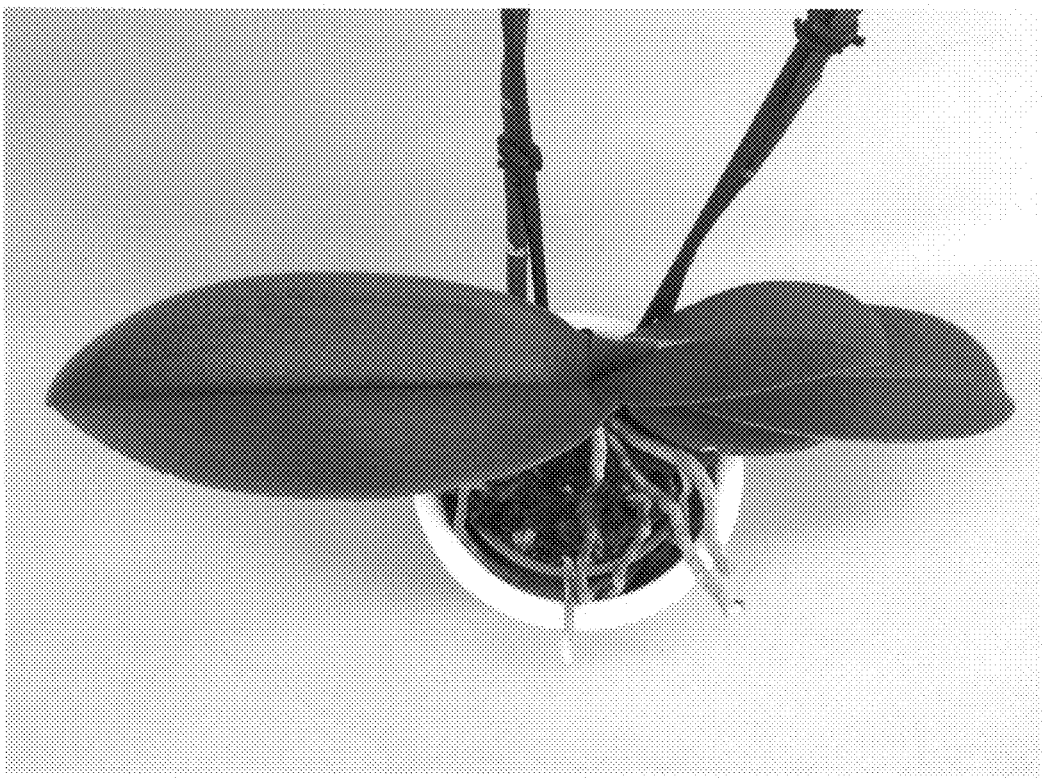
FIG. 3 shows a close-up of the leaves of 'PHALDUECH'.

The following detailed description sets forth the distinctive characteristics of 'PHALDUECH'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, The Netherlands. Observations and measurements were made in August 2016 on 50-week old plants which were planted from a nursery tray in 12 centimeter (diameter) pots and grown in a greenhouse between 27° C. to 29° C. for 30 weeks, continued by a cooling period of 8 weeks between 18° C. to 20° C. and 12 weeks in a greenhouse of 21° C.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALDUECH'.

Parentage:

*Female parent*.—*Phalaenopsis* cultivar '01-0274' (unpatented).

*Male parent*.—*Phalaenopsis* cultivar '22481-01' (unpatented).

Propagation:

*Type*.—Meristem tissue culture.

Roots:

*Root description*.—Greyed-green colored roots with branching lateral roots having light purple colored root tips.

Plant:

*Commercial crop time to flowering*.—Approximately 48 to 50 weeks from a rooted cutting to finish in a 12 cm pot.

*Growth habit of peduncle*.—Standard, green leaves, panicle.

*Height* (*from soil level to top of inflorescence*).—Approximately 34.0 cm to 44.0 cm.

*Width* (*measured from leaf tips*).—About 26.0 cm to 31.0 cm.

*Vigor*.—Strong.

Leaves:

*Mature leaves*.—Quantity per plant: 8 to 10 leaves are produced before flowering. Length (fully expanded): 13.0 cm to 16.0 cm. Width: 5.0 cm to 6.0 cm. Shape: Narrow oblong. Base shape: Moderately elongated. Apex: Unequal obtuse. Leaf blade angle with the petiole (measured from the horizontal position): Between 30 degrees and 45 degrees. Leaf margin: Entire. Color: Upper surface: RHS 147A. Lower surface: RHS 146B. Texture: Rough. Thickness: 3.0 mm to 3.3 mm. Venation: Pattern: Parallel. Color of the midvein: Upper surface: RHS 147A. Lower surface: RHS 146B.

Peduncle:

*Quantity per plant*.—1 to 3.

*Number of flowers per peduncle*.—11 to 18.

*Length*.—34.0 cm to 44.0 cm.

*Diameter*.—5.1 mm to 5 4.mm.

*Strength*.—Strong.

*Aspect*.—Upright.

*Texture*.—Smooth.

*Color*.—Green (RHS 146B) and slightly brown (RHS N199A) along the peduncle.

*Internode length*.—4.0 cm to 5.0 cm.

*Callosities*.—None.

Inflorescence description:

*Appearance*.—Upright to slightly pendant, panicle inflorescence with bilaterally symmetrical flowers that open in succession beginning with the lowermost flower.

*Inflorescence size*.—Height (from base to tip): 190.0 mm to 240.0 mm.

*Flowering time*.—First flowers can be expected 10 to 11 months after planting in a 12 cm (diameter) pot.

*Flower*.—Height: 55.0 mm to 60.0 mm. Diameter: 68.0 mm to 73.0 mm. Depth of lip: 19.0 mm to 21.0 mm.

*Flower longevity*.—On the plant: 9 to 12 weeks.

*Fragrance*.—Absent.

*Flower bud*.—Average size: Medium. Length: 17.0 mm to 19.0 mm. Width: 15.0 mm to 17.0 mm. Shape: Egg shaped. Color: Light green (RHS 145A).

*Petals*.—Arrangement: Open/free. Shape: Semi-circular. Apex: Rounded and asymmetric. Margin: Entire. Length (from base to tip): 31.0 mm to 33.0 mm. Width: 36.0 mm to 38.0 mm. Color (when fully opened): Upper surface: Basic color: White (RHS NN155C). Over color: Absent. Lower surface: Basic color: White (RHS NN155C). Over color: Absent.

*Dorsal sepal*.—Shape: Elliptical. Apex: Rounded to slightly emarginated and symmetric. Margin: Entire. Length (from base to tip): 33.0 mm to 35.0 mm. Width: 23.0 mm to 25.0 mm. Color (when fully opened): Upper surface: Basic color: White (RHS NN155C). Over color: Absent. Lower surface: Basic color: White (RHS NN155C). Over color: Absent.

*Lateral sepals*.—Shape: Ovate. Apex: Obtuse and asymmetric. Margin: Entire. Length (from base to tip): 35.0 mm to 37.0 mm. Width: 21.0 mm to 23.0 mm. Color (when fully opened): Upper surface: Basic color: White (RHS NN155C). Over color: Light green (RHS145C) at the base. Lower surface: Basic color: White (RHS NN155C). Over color: Light green (RHS 145C) at the base.

*Labellum* (*lip*).—Whiskers: Present. Length of whiskers: 11.0 mm to 13.0 mm. Color of whiskers: White (RHS NN155C). Pubescence on the lip: Absent.

*Lateral lobe*.—Shape: Type V (spatulate). Margin: Undulated. Length (from base to tip): 17.0 mm to 19.0 mm. Width: 13.0 mm to 15.0 mm. Color: White (RHS NN155C) and yellow (RHS 7B) on one side and a few brown (RHS 178B) stripes at the base.

*Apical lobe*.—Shape: Triangular. Margin: Entire. Length: 17.0 mm to 19.0 mm. Width: 20.0 mm to 22.0 mm. Color: White (RHS NN155C) and yellow (RHS 7C) at the base, diluting to brown (RHS 178B) towards the callus.

*Callus*.—Average size: Medium. Height: 0.6 cm to 0.8 cm. Length: 0.4 cm to 0.6 cm. Width: 0.3 cm to 0.5 cm. Color: Yellow (RHS 15A) and dotted (RHS 178B).

*Reproductive organs*.—Column: Length: 7.0 mm to 9.0 mm. Diameter: 4.9 mm to 5.1 mm. Color: White (RHS NN155C). Pollinia: Quantity: 2. Diameter: 0.9 mm to 1.1 mm. Color: Orange (RHS 26A). Ovary: Length: 6.0 mm to 8.0 mm. Diameter: 2.1 mm to 2.3 mm. Pedicel: Length: 24.0 mm to 26.0 mm. Diameter: 2.4 mm to 2.7 mm. Color: Green (RHS 145B) at the base and lighter green (RHS 145C to 145D) towards the flower; light purple (RHS 76C) by the flower.

Disease, pest, and stress resistance: No specific resistance or susceptibility observed to pathogens and pests common to *Phalaenopsis*.

Fruit and seeds: Fruit and seed development has not been observed on plants of the new *Phalaenopsis*.

COMPARISON WITH PARENTAL AND COMMERCIAL VARIETIES

'PHALDUECH' differs from female parent plant '01-0274' (unpatented) in that 'PHALDUECH' has a medium sized callus, lateral sepals with an even pattern and dorsal sepal lower surfaces with no overcolor, whereas '01-0274' has a small callus, lateral sepals with a dotted pattern and dorsal sepal lower surfaces with a purple overcolor. Additionally, 'PHALDUECH' has wider apical lobes and dorsal sepals than '01-0274'.

The male parent of 'PHALDUECH', cultivar '22481-01' (unpatented), is no longer in existence, so a meaningful comparison cannot be made.

'PHALDUECH' is most similar to the commercial *Phalaenopsis* plants named 'PHALDUXI' (U.S. Plant Pat. No. 25,680) and '23688-0005' (unpatented). 'PHALDUECH' differs from the commercial variety 'PHALDUXI' in that 'PHALDUECH' has lateral sepals with an even pattern, whereas 'PHALDUXI' has lateral sepals with a dotted pattern. Additionally, 'PHALDUECH' has larger flowers, wider apical lobes and shorter whiskers than 'PHALDUXI'.

'PHALDUECH' differs from similar variety '23688-005' in that 'PHALDUECH' has lateral sepals with an even pattern, spatulate shaped lateral lobes and a white column, whereas '23688-0005' has lateral sepals with a dotted pattern, weakly spatulate shaped lateral lobes and a light green column. Additionally, 'PHALDUECH' has larger flowers, wider apical lobes and longer whiskers than '23688-0005'.

I claim:

1. A new and distinct variety of *Phalaenopsis* plant named 'PHALDUECH', substantially as described and illustrated herein.

* * * * *